United States Patent [19]

Markussen et al.

[11] Patent Number: 4,916,212

[45] Date of Patent: Apr. 10, 1990

[54] DNA-SEQUENCE ENCODING BIOSYNTHETIC INSULIN PRECURSORS AND PROCESS FOR PREPARING THE INSULIN PRECURSORS AND HUMAN INSULIN

[75] Inventors: Jan Markussen, Herlev; Niels Fiil, Copenhagen; Mogens T. Hansen, Olstykke; Kjeld Norris, Birkerod, all of Denmark; Gustav Ammerer, East Seattle, Wash.; Lars Thim, Gentofte; Hans O. Voigt, Lyndby, both of Denmark

[73] Assignee: Novo Industri A/S, Bagsvaerd, Denmark

[21] Appl. No.: 739,123

[22] Filed: May 29, 1985

[30] Foreign Application Priority Data

May 30, 1984 [DK] Denmark .............................. 2665/84
Feb. 8, 1985 [DK] Denmark ................................ 582/85

[51] Int. Cl.$^4$ .................... C12N 15/00; C12N 12/00; C12N 1/20; C12P 21/00
[52] U.S. Cl. ................................ 530/303; 435/172.3; 435/69.4; 435/320; 435/252.33; 435/942; 435/256; 536/27; 935/13; 935/69
[58] Field of Search ...................... 435/253, 172.3, 681, 435/70, 320, 940, 252.33, 256, 942; 536/28, 27; 530/303, 808; 935/2, 17, 18, 13, 29, 40, 69

[56] References Cited

U.S. PATENT DOCUMENTS

| | | | |
|---|---|---|---|
| 4,343,898 | 8/1982 | Markussen | 435/70 |
| 4,431,740 | 2/1984 | Bell | 435/252.33 |
| 4,440,859 | 4/1984 | Rutter et al. | 435/172.3 |
| 4,615,974 | 10/1986 | Kingsman et al. | 435/172.3 |

FOREIGN PATENT DOCUMENTS

| | | |
|---|---|---|
| 146482B | 10/1980 | Denmark . |
| 0006694 | 1/1980 | European Pat. Off. . |
| 0037255 | 10/1980 | European Pat. Off. . |
| 0037723 | 10/1981 | European Pat. Off. . |
| 0040466 | 11/1981 | European Pat. Off. . |
| 0055945 | 7/1982 | European Pat. Off. . |
| 0060057 | 9/1982 | European Pat. Off. . |
| 0068701 | 1/1983 | European Pat. Off. . |
| 0070632 | 1/1983 | European Pat. Off. . |
| 0090433 | 10/1983 | European Pat. Off. . |
| 0121884 | 10/1984 | European Pat. Off. . |

OTHER PUBLICATIONS

Greene et al, Methods in Enzymology, vol. XLVII, 1977, pp. 170–172.

*Primary Examiner*—Thomas G. Wiseman
*Assistant Examiner*—Patricia Carson
*Attorney, Agent, or Firm*—Morris Fidelman; Franklin D. Wolffe

[57] ABSTRACT

Human insulin precursors containing the peptide chain B(1-29)–A(1-21) of human insulin and derivatives thereof with a bridging chain connecting the carboxyl terminus of the B(1-29)-chain with the amino terminus of the A(1-21)-chain are prepared by culturing a yeast host transformed with a replicable expression vehicle capable of expressing a DNA-sequence encoding the insulin precursor. The bridging chain is preferably relatively short and contains preferably from 2 to 8 amino acid residues. The bridging chain must not contain two adjacent basic amino acid residues (Lys or Arg) and has one Lys or Arg connected to the amino terminus of the A(1-21)-chain. Human insulin is prepared from the insulin precursors by in vitro conversion.

32 Claims, 8 Drawing Sheets

DNA-SEQUENCE ENCODING BIOSYNTHETIC INSULIN PRECURSORS AND PROCESS FOR PREPARING THE INSULIN PRECURSORS AND HUMAN INSULIN

This invention relates to biosynthetic insulin. More specifically, the invention is directed to DNA-sequences encoding biosynthetic insulin precursors and to the preparation of such insulin precursors which are convertible into biosynthetic human insulin by in vitro conversion.

BACKGROUND OF THE INVENTION

In the past insulin has been synthezised (from synthetic A- and B-chains) or re-synthesized (from naturally derived A- and B-chains) by combining the two chains in an oxidation process whereby the 6 cysteine sulfhydryl groups of the reduced chains (4 in the A-chain, 2 in the B-chain) are converted into disulfide bonds. By this method disulfide bonds are formed largely at random, meaning that the yield of insulin with disulfide bridges correctly positioned between cysteine residues A-6 and A-11, A-7 and B-7, and A-20 and B-19, respectively, is very low.

Following the discovery of proinsulin as a biological precursor of insulin it was observed that the A- and B-polypeptide moieties of the linear-chain totally reduced proinsulin (those moieties corresponding to the A- and B-chains of insulin, respectively) could be oxidatively combined with much less randomization of the disulfide bonds to give a substantially higher yield of correctly folded proinsulin as compared with the combination of free A- and B-chains (D. F. Steiner et al.: Proc. Nat. Acad. Sci. 60 (1968), 622). Albeit high yields were obtained only at proinsulin concentrations too low to make the process feasible on a preparative scale, the function of the C- (i.e. connecting peptide) moiety of the B-C-A polypeptide sequence of proinsulin, namely that of bringing the 6 cysteine residues into spatial positions favorable for correct oxidation into proinsulin, was clearly demonstrated.

The proinsulin formed may function as an in vitro precursor of insulin in that the connecting peptide is removable by enzymatic means (W. Kemmler et al.: J. Biol. Chem. 246 (1971), 6786).

Subsequently it has been shown that proinsulin-like compounds having shorter linking moieties than the C-peptide and flanked at both ends by specific enzymatic or chemical cleavage sites (the so-called miniproinsulins (A. Wollmer et al., Hoppe-Seyler's Z. Physiol. Chem. 355 (1974), 1471-1476 and Dietrich Brandenburg et al., Hoppe-Seyler's Z. Physiol. Chem. 354 (1973), 1521-1524)) may also serve as insulin precursors.

Endeavours to provide biosynthetic insulins, particularly that identical to the human species, have followed the same strategic pathways as those to synthetic insulin. The insulin A- and B-chains have been expressed in separate host organisms, isolated therefrom and then combined as described supra (R. E. Chance et al.: Diabetes Care 4 (1982), 147). Microorganisms have been transformed with cloning vectors encoding preproinsulin or proinsulin which may be secreted as such (W. Gilbert et al.: European Patent Publ. No. 6694) or accumulated intracellularly as hybrid gene products (D. V. Goeddel et al.: European Patent Publ. No. 55945). The miniproinsulin pathway has also been attempted (D. V. Goeddel, supra).

Procuring the A- and B-chains in separate fermentation processes followed by combination of the chains is inherently impractical. The dual fermentation inconvenience may be overcome by choosing the proinsulin or miniproinsulin strategy. However, the use of a proinsulin as the biosynthetic insulin precursor may entail certain disadvantages. The proinsulin, whether excreted into the fermentation liquid as such or accumulated intracellularly in the host organism, possibly as a hybrid gene product, is likely to contain substantially randomized disulfide bonds. The refolding of such "scrambled" products into correctly folded proinsulin may be conducted either directly (H.—G. Gattner et al.: Danish Patent Application No. 4523/83) or via the single chain hexa-S-sulfonate (F. B. Hill: European Patent Publ. No. 37255). The refolding process usually entails some degree of polymerization and hence the inconvenience of using laborious purification steps during recovery.

In addition, insulin precursors of the proinsulin type are prone to undergo enzymatic degradation, either within the host cells or following its excretion into the fermentation broth. In yeast it has been shown that human proinsulin is particularly sensitive to enzymatic cleavages at the two dibasic sequences (Arg31–Arg32 and Lys64–Arg65). Apparently these cleavages occur before the establishment of the S—S bridges, resulting in the formation of C-peptide, A-chain and B-chain.

OBJECT OF THE INVENTION AND SUMMARY THEREOF

The object of the present invention is to circumvent these disadvantages by devising biosynthetic insulin precursors which are generated largely with correctly positioned disulfide bridges between the A- and B-moieties and, furthermore, substantially more resistant to proteolytic degradation than the biosynthetic insulin precursors known heretofore.

A single chain insulin precursor consisting of a shortened insulin B-chain from $Phe^{B1}$ to $Lys^{B29}$ continuing into a complete A-chain from $Gly^{A1}$ to $Asn^{A21}$, B(1-29)-A(1-21), is known (Jan Markussen, "Proteolytic degradation of proinsulin and of the intermediate forms",: Proceedings of the Symposium on Proinsulin, Insulin and C-Peptide, Tokushima, 12–14 July, 1978, Editors: S. Baba et al.). This insulin precursor B(1-29)-A(1-21) is prepared by a semisynthetic process from porcine insulin. First the insulin B(1-29) and A(1-21) chains were prepared and coupled to form a linear peptide B(1-29)-A(1-21). This compound in the hexathiol form was oxidized in vitro rendering the single chain des-(B30) insulin molecule.

The present invention is based on the surprising discovery that the above single chain insulin precursor B(1-29)-A(1-21) and derivatives thereof with a bridging chain connecting the carboxyl terminus of the B(1-29)-chain with the amino terminus of the A(1-21)-chain are expressed in high yields and with correctly positioned disulfide bridges when culturing yeast strains transformed with DNA-sequences encoding such insulin precursors are cultured.

According to a first aspect of the present invention there is provided a DNA-sequence encoding insulin precursors of the formula

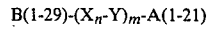             I wherein $X_n$ is a peptide chain with n amino acid residues, Y is Lys or Arg, n is an integer from 0 to 33, m is 0 or 1, B(1-29) is a shortened B-chain of human insulin from $Phe^{B1}$ to $Lys^{B29}$ and A(1-21) is the A chain of human insulin, with the proviso that the peptide chain -$X_n$-Y- does not contain two adjacent basic amino acid residues (i.e. Lys and Arg).

Preferred insulin precursors of the above formula I are B(1-29)-A(1-21), i.e. m=0 in formula I, and compounds with a relative short bridging chain between the B(1-29)- and the A(1-21)-chain.

When m=1, then n is preferably 1-33, more preferably 1-15, 1-8 or 1-5 and most preferably 1-3 or 1-2. X may preferably be selected from the group consisting of Ala, Ser and Thr, the individual X's being equal or different. Examples of such preferred compounds are B(1-29)-Ser-Lys-A(1-21) and B(1-29)-Ala-Ala-Lys-A(1-21).

According to a second aspect of the present invention there is provided a replicable expression vehicle capable of expression of a DNA-sequence comprising a sequence encoding the insulin precursors of formula I in yeast.

The expression vehicle may be a plasmid capable of replication in the host microorganism or capable of integration into the host organism chromosome. The vehicle employed may code for expression of repeated sequence of the desired DNA-sequence, each separated by selective cleavage sites.

According to a third aspect of the present invention there is provided a process for producing insulin precursors of formula I in yeast wherein a transformant yeast strain including at least one expression vehicle capable of expressing the insulin precursors is cultured in a suitable nutrient medium followed by isolation of the insulin precursors.

According to a fourth aspect of the present invention there are provided novel human insulin precursors. Such novel human insulin precursors have the following general formula

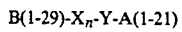   II in which the different symbols have the above mentioned definitions. Preferred novel insulin precursors are B(1-29)-Ser-Lys-A(1-21) and B(1-29)-Ala-Ala-Lys-A(1-21).

According to a fifth aspect of the present invention there is provided a yeast strain transformed with an expression vehicle capable of expressing a DNA-sequence comprising a sequence encoding the above insulin precursors in yeast.

The insulin precursors may be expressed with additional protein proceeding the insulin precursor. The additional protein may have the function of protecting the insulin precursor against, e.g. in vivo degradation by endogeneous enzymes or of providing information necessary to transport the desired protein into the periplasmic space and finally across the cell wall into the medium.

The additional protein contains a selective cleavage site adjacent to the N-terminal of the B(1-29)-chain of the insulin precursors enabling subsequent splitting off of the additional protein either by the microorganism itself or by later enzymatical or chemical cleavage.

Accordingly the present invention includes a DNA-sequence encoding the above insulin precursors and further comprising an additional DNA-sequence positioned upstream to the sequence encoding the insulin precursors and encoding an additional amino acid-sequence containing a selective cleavage site adjacent to the N-terminal of the B(1-29)-chain of the insulin precursors.

According to a preferred embodiment of the present invention the additional amino acid sequence comprises at least one basic amino acid adjacent to the N-terminal of the B(1-29)-chain of the insulin precursor.

When the insulin precursor is expressed in yeast the additional amino acid-sequence may contain two basic amino acids (e.g. Lys-Lys, Arg-Arg, Lys-Arg or Arg-Lys) adjacent to N-terminal of the B(1-29)-chain of the insulin precursor, yeast being able to cleave the peptide bond between the basic amino acids and the precursor. Also a Glu-Ala or Asp-Ala cleavage site adjacent to the desired protein enables separation of the additional amino acid sequence by the yeast itself by means of a dipeptidase enzyme produced by the yeast.

The insulin precursors may be secreted with an amino acid-sequence linked to the B(1-29)-chain of the precursors provided that this amino acid sequence contains a selective cleavage site adjacent to the B(1-29)-chain for later splitting of the superfluous amino acid sequence. If the insulin precursors do not contain methionine cyanogen bromide cleavage at methionine adjacent to the desired protein would be operative. Likewise, arginine- and lysine-cleavage sites adjacent to the desired protein enables cleavage with trypsinlike proteases.

For secretion purposes the DNA-sequence encoding the insulin precursors may be fused to an additional DNA-sequence coding for a signal peptide. The signal peptide is cleaved off by the transformant microorganism during the secretion of the expressed protein product from the cells ensuring a more simple isolation of the desired product. The secreted product may be the insulin precursor or may contain an additional N-terminal amino acid-sequence to be removed later as explained above.

Secretion may be provided by including in the expression vehicle the yeast MFα1 leader sequence (Kurjan, J. and Herskowitz, I., Cell 30, (1982), 933-943) and according to a further preferred embodiment of the present invention the additional amino acid-sequence positioned upstream to the sequence encoding the insulin precursors comprises the yeast MFα1 leader coding sequence or part thereof.

The expression of the desired DNA-sequence will be under control of a promoter sequence correctly positioned to the DNA-sequence encoding the desired protein product to result in expression of the desired protein in the host organism. Preferably a promoter from a gene indigenous to the host organism may be used. The DNA-sequence for the desired protein will be followed by a transcription terminator sequence, preferably a terminator sequence from a gene indigenous to the host organism. If yeast is used as host organism the promoter and terminator sequences are preferably the promoter and terminator of the triose phosphase isomerase (TPI) gene, respectively.

Other promoters may be utilized such as the phosphoglycerate kinase (PGK1)- and the MFα1-promoter.

The present invention further comprises a method for preparing human insulin by which a yeast strain is transformed with a replicable expression vehicle comprising a DNA-sequence encoding the insulin precursors of the above formula I, the transformed yeast strain is cultured in a suitable nutrient medium, the insulin precursors are recovered from the culture medium and converted in vitro into human insulin.

The insulin precursors according to the present invention may be converted into mature human insulin by transpeptidation with an L-threonine ester in the presence of trypsin or a trypsin derivative as described in the specification of U.S. Pat. No. 4,343,898 (the disclosure of which is incorporated by reference hereinto) followed by transformation of the threonine ester of human insulin into human insulin by known processes.

If the insulin precursors are secreted with an additional amino acid sequence adjacent to the N-terminal of the B(1-29)-chain such amino acid sequence should either be removed in vitro before the transpeptidation or should contain at least one basic amino acid adjacent to the N-terminal of the B(1-29)-chain as trypsin will cleave the peptide bond between the basic amino acid and the amino group of Phe$^{B1}$ during the transpeptidation.

BRIEF DESCRIPTION OF THE DRAWINGS

The accompanying drawings illustrate a preferred embodiment of the present invention.

Figure 1:
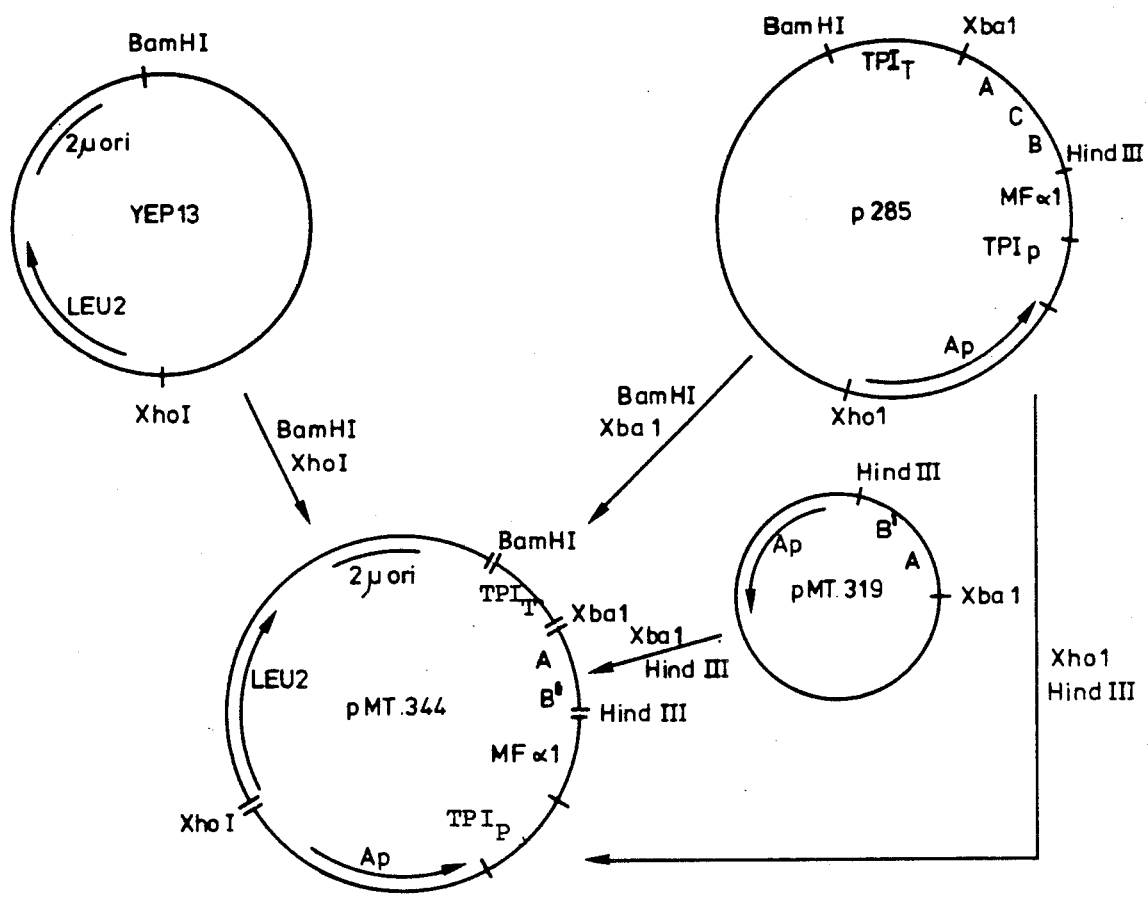
FIG. 1 illustrates the preparation of plasmid pMT344.

In the drawings and part of the following description the expression B' is used instead of B(1-29) and A instead of A(1-21). Accordingly the expression B'A is equivalent to the expression B(1-29)-A(1-21).

DETAILED DESCRIPTION

1. Preparation of a gene coding for human proinsulin B-C-A

Total RNA purified (Chirgwin, J. M. Przybyla, A. E., McDonald, R. J. & Rutter, W. J., Biochemistry 18, (1979) 5294–5299) from human pancreas was reverse transcribed (Boel, E., Vuust, J., Norris, F., Norris, K., Wind, A., Rehfeld, J. F. & Marcker, K. A., Proc. Natl. Acad. Sci. USA 80, (1983) 2866–2869) with AMV reverse transcriptase and d(GCTTTATT-CCATCTCTC) as 1. strand primer. After preparative urea-polyacrylamide gel purification of the human proinsulin cDNA, the second strand was synthesized on this template with DNA polymerase large fragment and d(CAGATCACTGTCC) as 2nd strand primer. After S1 nuclease digestion the human proinsulin ds. cDNA was purified by polyacrylamide gel electrophoresis, tailed with terminal transferase and cloned in the PstI site on pBR327 (Sorberon et al., Gene 9, (1980), 287–305) in E. coli. A correct clone harbouring a plasmid containing a gene encoding human proinsulin B-C-A was identified from the recombinants by restriction endonuclease analysis and confirmed by nucleotide sequencing (Maxam, A., & Gilbert, W., Methods in Enzymology, 65 (1980), 499–560. Sanger, F., Nicklen, S. and Coulson, A. R., Proc. Natl. Acad. Sci. USA 74, (1977), 5463–5467).

2. Preparation of genes coding for precursors of human insulin

The gene encoding B(1-29)-A(1-21) of human insulin was made by site specific mutagenesis of the human proinsulin sequence with a 75 bp in frame deletion in the C-peptide coding region inserted into a circular single stranded M-13 bacteriophage vector. A modified procedure (K. Norris et al., Nucl. Acids. Res. 11 (1983) 5103–5112) was used in which a chemically synthesized 19-mer deletion primer was annealed to the M13 template. After a short enzymatic extension reaction a "universal" 15-mer M13 dideoxy sequencing primer was added followed by enzymatic extension and ligation. A double stranded restriction fragment (BamHl-Hind III) was cut out of the partly double stranded circular DNA and ligated into pBR322 cut with BamHI and Hind III.

The obtained ligation mixture was used to transform E. coli and transformants harbouring a plasmid pMT319 containing the gene encoding B(1-29)-A(1-21) of human insulin were identified.

Genes encoding B(1-29)-Ala-Ala-Lys-A(1-21) and B(1-29)-Ser-Lys-A(1-21) were made accordingly by insertion of a fragment encoding MFα1-B-C-A in the M-13 bacteriophage and site specific mutagenesis of the human proinsulin sequence with chemically synthesized 30-mer and 27-mer deletion primers, respectively, and the above mentioned "universal" 15-mer M13 dideoxy sequencing primer. A double stranded restriction fragment (XbaI-EcoRl) was cut out of the partly double stranded circular DNA and ligated into pUC13 and pT5, respectively. By transformation and retransformation of E. coli, transformants harbouring a plasmid pMT598 containing the gene encoding B(1-29)-Ala-Ala-Lys-A(1-21) and pMT630 containing the gene encoding B(1-29)-Ser-Lys-A(1-21) were identified.

A gene encoding B(1-29)-Thr-Arg-Glu-Ala-Glu-Asp-Leu-Gln-Lys-A(1-21) was made in a similar way as described above by insertion of a fragment encoding MFα1-B(1-29)-A(1-21) in a M13 mp11 bacteriophage and site specific mutagenesis of the B(1-29)-A(1-21) sequence with a chemically synthesized 46-mer deletion primer (5'-CACACCCAAGACTAAAGAAGCT-GAAGACTTGCAAAGAGGCATTGTG-3') and the "universal" primer. Also, by a similar procedure a gene encoding B(1-29)-Thr-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-A(1-21) was constructed.

3. Plasmid constructions

The gene encoding B(1-29)-A(1-21) of human insulin (B'A) was isolated as a restriction fragment from pMT319 and combined with fragments coding for the TPI promoter (TPI$_P$) (T. Alber and G. Kawasaki. Nucleotide Sequence of the Triose Phosphate Isomerase Gene of Saccharomyces cerevisiae. J. Mol. Applied Genet. 1 (1982) 419–434), the MFα1 leader sequence (J. Kurjan and I. Herskowitz,. Structure of a Yeast Pheromone Gene (MFα): A Putative α-Factor Precursor Contains four Tandem Copies of Mature α-Factor. Cell 30 (1982) 933–943) and the transcription termination sequence from TPI of S. cerevisiae (TPI$_T$). These fragments provide sequences to ensure a high rate of transcription for the B'A encoding gene and also provide a presequence which can effect the localization of B'A into the secretory pathway and its eventual excretion into the growth medium. This expression unit for B'A (TPI$_P$-MFα1 leader—B'A—TPI$_T$ was then placed on a plasmid vector containing the yeast 2μ origin of replication and a selectable marker, LEU 2, to give pMT344, a yeast expression vector for B'A.

During in vivo maturation of α-factor in yeast, the last (C-terminal) six amino acids of the MFα1 leader peptide (Lys-Arg-Glu-Ala-Glu-Ala) are removed from the α-factor precursor by the sequential action of an endopeptidase recognizing the Lys-Arg sequence and an aminodipeptidase which removes the Glu-Ala residues (Julius, D. et al. Cell 32 (1983) 839–852). To eliminate the need for the yeast aminodipeptidase, the sequence coding for the C-terminal Glu-Ala-Glu-Ala of the MFα1 leader was removed via in vitro mutagenesis. The resulting yeast expression plasmid, pMT475, contains the insert coding for TPI$_P$-MFα1 leader (minus Glu-Ala-Glu-Ala)—B'A—TPI$_T$.

In a preferred construction the modified expression unit was transferred to a stable, high copy number yeast plasmid CPOT, (ATCC No. 39685), which can be selected merely by the presence of glucose in the growth medium. The resulting yeast expression vector for B'A was numbered pMT479.

The fragment encoding MFα1 leader (minus Glu-Ala-Glu-Ala)-B(1-29)-Ala-Ala-Lys-A(1-21) was isolated as a restriction fragment from pMT598 and combined with fragments coding for the TPI promoter and the TPI terminator and transferred to the above mentioned high copy number yeast plasmid CPOT. The resulting yeast expression vector for B(1-29)-Ala-Ala-Lys-A(1-21) was numbered pMT610.

The fragment containing the insert TPI$_P$-MFα1 leader (minus Glu-Ala-Glu-Ala)-B(1-29)-Ser-Lys-A(1-21)-TPI$_T$ was isolated as a restriction fragment from pMT630 and transferred into CPOT. The resulting yeast expression vector for B(1-29)-Ser-Lys-A(1-21) was numbered pMT639.

The fragment containing the insert TPI$_P$-MFα1 leader (minus Glu-Ala-Glu-Ala)-B(1-29)-Thr-Arg-Glu-Ala-Glu-Asp-Leu-Gln-Lys-A(1-21)-TPI$_T$ was inserted into a high copy number yeast plasmid DPOT, being a CPOT derivative containing a SphI-BamHI-fragment of pBR322 inserted into a SpHI-BamHI fragment of CPOT. The resulting yeast expression vector for B(1-29)-Thr-Arg-Glu-Ala-Glu-Asp-Leu-Gln-Lys-A(1-21) was numbered p1126.

4. Transformation

Plasmids pMT344 and pMT475 were transformed into *S. cerevisiae* leu 2 mutants by selection for leucin prototrophy as described by Hinnen et al. (A. Hinnen, J. B. Hicks and G. R. Fink. Transformation of Yeast. Proc. Nat. Aca. Sci. 75 (1978) 1929).

Plasmids pMT479, pMT610, pMT639 and p1126 were transformed into *S. cerevisiae* strains carrying deletions in the TPI gene by selecting for growth on glucose. Such strains are normally unable to grow on glucose as the sole carbon source and grow very slowly on galactose lactate medium. This defect is due to a mutation in the triose phosphate isomerase gene, obtained by deletion and replacement of a major part of this gene with the *S. cerevisiae* LEU 2 gene. Because of the growth deficiencies there is a strong selection for a plasmid which contains a gene coding for TPI. pMT479 contains the *Schizo. pombe* TPI gene.

5. Expression of human insulin precursors in yeast

Expression products of human insulin type were measured by radioimmunoassay for insulin as described by Heding, L. (Diabetologia 8, 260–66, 1972) with the only exception that the insulin precursor standard in question was used instead of an insulin standard. The purity of the standards were about 98% as determined by HPLC and the actual concentration of peptide in the standard was determined by amino acid analysis. The expression levels of immunoreactive human insulin precursors in the transformed yeast strains are summarized in Table 1.

TABLE 1

Expression levels of immunoreactive human insulin precursors in yeast.

| Yeast strain | Plasmid | Construct | Immunoreactive insulin precursor (nmol/l supernatant) |
|---|---|---|---|
| MT 350 (DSM 2957) | pMT 344 | B(1-29)-A(1-21) | 100 |
| MT 371 (DSM 2958) | pMT 475 | B(1-29)-A(1-21) | 192 |
| MT 519 (DSM 2959) | pMT 479 | B(1-29)-A(1-21) | 2900 |
| MT 620 (DSM 3196) | pMT 610 | B(1-29)-Ala—Ala—Lys-A(1-21) | 1200–1600 |
| MT 649 (DSM 3197) | pMT 639 | B(1-29)-Ser—Lys-A(1-21) | 1600 |
| ZA 426 | p1126 | B(1-29)-Thr—Arg—Glu—Ala—Glu—Asp—Leu—Gln—Lys-A(1-21) | 200 |

The isolation and characterization of expression products are given in Examples 7–9 and 12–13.

6. Conversion of human insulin precursor into B30 esters of human insulin

The conversion of the human insulin precursors into human insulin esters can be followed quantitatively by HPLC (high pressure liquid chromatography) on reverse phase. A 4×300 mm "μBondapak C18 column" (Waters Ass.) was used and the elution was performed with a buffer comprising 0.2M ammonium sulphate (adjusted to a pH value of 3.5 with sulphuric acid) and containing 26–50% acetonitrile. The optimal acetonitrile concentration depends on which ester one desires to separate from the insulin precursor. In case of human insulin methyl ester separation is achieved in about 26% (v/v) of acetonitrile.

Before the application on the HPLC column the proteins in the reaction mixture were precipitated by addition of 10 volumes of acetone. The precipitate was isolated by centrifugation, dried in vacuo, and dissolved in 1M acetic acid.

EXPERIMENTAL PART

Example 1

Construction of a gene coding for B(1-29)-A(1-21)insulin

Materials and Methods

"Universal" 15-mer M13 dideoxy sequencing primer d(TCCCAGTCACGACGT), T4 DNA ligase and restriction enzymes were obtained from New England Biolabs. DNA polymerase I "Klenow fragment" and T4 polynucleotide kinase were purchased from P-L Biochemicals. ($\gamma$-$^{32}$P)-ATP (7500 Ci/mmol) was obtained from New England Nuclear. The support for oligonucleotide synthesis was 5'-O-dimethoxytrityl N$^2$-isobutyryldeoxyguanosine bound via a 3'-O-succinyl group to aminomethylated 1% crosslinked polystyrene beads from Bachem.

Construction of M13 mp10 insHX PstΔphage:

The M13 mp10 derived phage mp10 insHX was constructed by cloning of the 284 bp large proinsulin coding Hind III-XbaI fragment, isolated from p285, into Hind III-XbaI cut M13 mp10 RF. M13 mp10 RF is available from P-L Biochemicals, Inc. Milwaukee, Wis. (Catalogue No. 1541).

M13 mp10 insHXΔPst was constructed from mp10 insHX,RF by complete PstI digestion followed by ligation and transformation of E. coli JM103. The resulting phage harbours the human proinsulin coding sequences, with a 75 bp in frame deletion in the C-peptide coding region. Single stranded phage was prepared as described (Messing, J. and Vieira, J. (1982) Gene 19, 269–276).

Oligodeoxyribonucleotide synthesis

The 19-mer deletion primer d(CACACCCAAGG-GCATTGTG) was synthesized by the triester method on a 1% crosslinked polystyrene support (Ito, H., Ike, Y., Ikuta, S., and Itakura, K. (1982) Nucl. Acids Res. 10, 1755–1769). The polymer was packed in a short column, and solvents and reagents were delivered semi-automatically by means of an HPLC pump and a control module. The oligonucleotide was purified after deprotection by HPLC on a LiChrosorb RP18 column (Chrompack (Fritz, H.-J., Belagaje, R., Brown, E. L., Fritz, R. H., Jones, R. A., Lees, R. G., and Khorana, H. G. (1978) Biochemistry 17, 1257–1267).

5'-$^{32}$P-labelling of oligodeoxyribonucleotide

The 19-mer was labelled at the 5'end in a 60 $\mu$l reaction mixture containing 50 mM Tris-HCl at pH 9.5, 10 mM MgCl$_2$, 5 mM DTT, 0.4% glycerol, 120 pmole ATP, 50 $\mu$Ci of ($\gamma$-$^{32}$P)-ATP (10 pmole), 120 pmole of oligonucleotide and 30 units of T4 polynucleotide kinase. The reaction was carried out at 37° C. for 30 min., and terminated by heating at 100° C. for 3 min. The labelled oligonucleotide was separated from unreacted ($\gamma$-$^{32}$P)-ATP by chromatography on a column (1×8 cm) of Sephadex G50 superfine in 0.05M triethylammonium bicarbonate at pH 7.5.

For colony hybridization the oligonucleotide was labelled without the addition of "cold" ATP as described (Boel, E., Vuust, J., Norris, F., Norris, K., Wind, A., Rehfeld, J., and Marcker, K. (1983) Proc. Natl. Acad. Sci. USA 80, 2866–2869).

Oligodeoxyribonucleotide primed DNA synthesis

Single stranded M13 mp10 insHXΔPst (0.4 pmole was incubated with the 19-mer 5'-($^{32}$P)-labelled oligodeoxyribonucleotide primer (10 pmole) in 20 $\mu$l of 50 mM NaCl, 20 mM Tris-HCl pH 7.5, 10 mM MgCl$_2$ and 1 mM DTT for 5 min. at 55° C. and annealed for 30 min. at 11° C. Then 9 $\mu$l of d-NTP-mix consisting of 2.2 mM of each dATP, dCTP, dGTP, dTTP, 20 mM Tris-HCl, pH 7.5, 10 mM MgCl$_2$, 50 mM NaCl, 1 mM DTT was added followed by 7 units of E. coli DNA polymerase I (Klenow). The mixture was kept for 30 min. at 11° C. and heated for 10 min. at 65° C. 15-mer universal primer for dideoxy sequencing (4 pmole) was added and the mixture heated at 65° C. for an additional minute. After cooling to 11° C. 26 $\mu$l of solution containing 20 mM Tris-HCl pH 7.5, 10 mM MgCl$_2$, 10 mM DTT, 0.8 mM of each dATP, dCTP, dGTP, dTTP, 2.4 mM ATP and 10$^3$ units of T4 ligase was added followed by 9.5 units of E. coli DNA polymerase I (Klenow). The final volume of the mixture was 64 $\mu$l. After incubation for 3 hours at 11° C. 20 $\mu$l 4M sodium acetate was added, and the volume adjusted to 200 $\mu$l with TE-buffer (10 mM Tris-HCl pH 8.0, 1 mM EDTA).

The mixture was extracted twice with phenol/chloroform. 0.9 $\mu$g (0.3 pmole) of the purified large fragment of pBR322 cleaved with BamHI and Hind III was added as carrier DNA. After ether extraction of the aqueous phase, the DNA was isolated by ethanol precipitation.

Endonuclease digestion

The DNA, prepared as described above, was digested respectively with 16 and 20 units of restriction endonucleases BamHI and Hind III in a total volume of 22 $\mu$l of buffer (50 mM NaCl, 10 mM Tris-HCl, pH 7.5, 10 mM MgCl$_2$, 1 mM DDT, 4 mM spermidine). The mixture was extracted with phenol/chloroform followed by ether and the DNA was isolated by ethanol precipitation and then dissolved in 12 $\mu$l H$_2$O. 2 $\mu$l was used for electrophoresis on a 7M urea 6% polyacrylamide gel.

Ligation

To a part of the DNA (5 $\mu$l) was added a new portion of the purified large fragment of pBR322 cut with BamHI and Hind III (0.38 $\mu$g) and 400 units of T4 DNA ligase, in a total volume of 41 $\mu$l containing 66 mM Tris-HCl, pH 7.4, 10 mM MgCl$_2$, 1 mM ATP, 10 mM DDT, 40 $\mu$g/ml gelatine. Ligation was performed at 16° C. for 16 hours.

Transformation 20.5 $\mu$l of the ligation mixture was used to transform CaCl$_2$ treated E. coli MC 1000 (r$^-$, m$^+$). The bacteria were plated on LB-agar plates and selected for resistance to ampicillin (100 $\mu$g/ml). 2.6×10$^3$ colonies per pmole of M13 mp10 insHXΔPst were obtained.

Colony hybridization 123 transformed colonies were picked onto fresh ampicillin plates and grown overnight at 37° C. Colonies were transferred to Whatman 540 filter paper and fixed (Gergen, J. P., Stern, R. H., and Wensink, P. C. (1979), Nucl. Acids Res. 7, 2115–2136). A prehybridization was performed in a sealed plastic bag with 6 ml of 0.9M NaCl, 0.09M Tris-HCl pH 7.5 0.006M EDTA, 0.2% Ficoll, 0.2% polyvinylpyrrolidone, 0.2% bovine serum albumin, 0.1% SDS and 50 $\mu$g/ml salmon sperm DNA for 2 hours at 65° C. Then 8.5×10$^6$ cpm of $^{32}$P-labelled 19-mer was added and hybridization performed at 45° C. overnight. The filter was washed with 0.9M NaCl, 0.09M sodium citrate three times at 0° C. for 5 min. and was then autoradiographed and washed once at 45° C. for 1 min. and autoradiographed again. After washing at 45° C., identification of 3 colonies containing mutated plasmid was possible.

Endonuclease analysis of mutated plasmids

Plasmids from the supposed mutant colonies were prepared by a rapid method (Ish-Horowicz, D. and Burke, J. F. (1981), Nucl. Acids Res. 9, 2989–2998), digested with a mixture of BamHI and Hind III and then analysed by electrophoresis on a 2% agarose gel. The presence of a 179 bp fragment confirmed that the 3 colonies contained mutant plasmid.

Retransformation

The colonies identified as "mutant" contain plasmids which are the progeny of a heteroduplex. Pure mutant could be obtained by retransformation of $CaCl_2$ treated E. Coli MC1000 ($r^-$, $m^+$) with plasmid from 2 of the mutant colonies. From each plate 5 ampicillin resistant clones were isolated, plasmid DNA was prepared and analysed by endonuclease cleavage as mentioned above. 3 out of 5 and 5 out of 5 respectively were shown to be pure mutant. One plasmid pMT319 was selected for further use.

DNA sequence analysis

5 μg of pMT319 was cleaved with BamHI under standard conditions, phenol extracted and ethanol precipitated. Filling in of the BamHI sticky ends was performed with Klenow DNA polymerase I, dCTP, dGTP, dTTP, and $\alpha$-$^{32}$P-dATP.

After phenol extraction and ethanol precipitation the DNA was digested with EcoRI. The $^{32}$-P labelled fragment with the deletion was purified by electrophoresis on a 2% agarose gel and sequenced by the Maxam-Gilbert method (Maxam, A. and Gilbert, W. (1980) Methods in Enzymology 65, 499–560).

EXAMPLE 2

Construction of a yeast plasmid pMT344 for expression of B(1-29)-A(1-21) of human insulin (B'A)

Plasmid pMT319 containing the gene coding for B'A and constructed as explained above was cut with restriction enzymes Hind III and XbaI and a 0.18 kb fragment was isolated (T. Maniatis, E. F. Fritsch, and J. Sambrook. Molecular Cloning. Cold Spring Harbor Press 1982) from a 2% agarose gel. Similarly a fragment (6.5 kb XhoI-Hind III) containing the S. cerevisiae TPI promotor ($TPI_P$) (T. Alber and G. Kawasaki. Nucleotide Sequence of the Triose Phosphate Isomerase Gene of Saccharomyces cerevisiae, J. Mol. Applied Genet. 1 (1982) 419–434) and the MFα1 leader sequence (J. Kurjan and I. Herskowitz, Structure of a Yeast Pheromone Gene (MFα): A Putative α-Factor Precursor Contains four Tandem Copies of Mature α-Factor. Cell 30 (1982) 933–943) was isolated from plasmid p285 constructed as described in U.S.-patent application Ser. No. 547,748 of Nov. 1, 1983. P285 contains the insert $TPI_P$-MFα1 leader -B-C-A- $TPI_T$ and was deposited in yeast strain Z33 (ATCC No. 20681). A fragment (0.7 kb XbaI-BamHI) containing the TPI transcription termination sequences ($TPI_T$) (T. Alber and G. Kawasaki, Nucleotide Sequence of the Triose Phosphate Isomerase Gene of Saccharomyces cerevisiae. J. Mol. Applied Genet. 1 (1982) 419–434) was also isolated from p285. Finally a 5.4 kb XhoI-BamHI fragment was isolated from the yeast vector YEp13 (J. R. Broach. Construction of High Copy Yeast Vectors Using 2 μm Circle Sequences. Methods Enzymology 101 (1983) 307–325). The above four fragments were ligated (T. Maniatis, E. F. Fritsch, and J. Sambrook. Molecular Cloning. Cold Spring Harbor Press 1982) and transformed into E. coli (T. Maniatis, E. F. Fritsch, and J. Sambrook. Molecular Cloning. Cold Spring Harbor Press 1982) selecting for ampicillin resistance. Plasmids were isolated from the transformants and the structure of one of these, pMT344, verified by restriction mapping. The construction and main features of pMT344 are outlined in FIG. 1.

EXAMPLE 3

Figure 2:
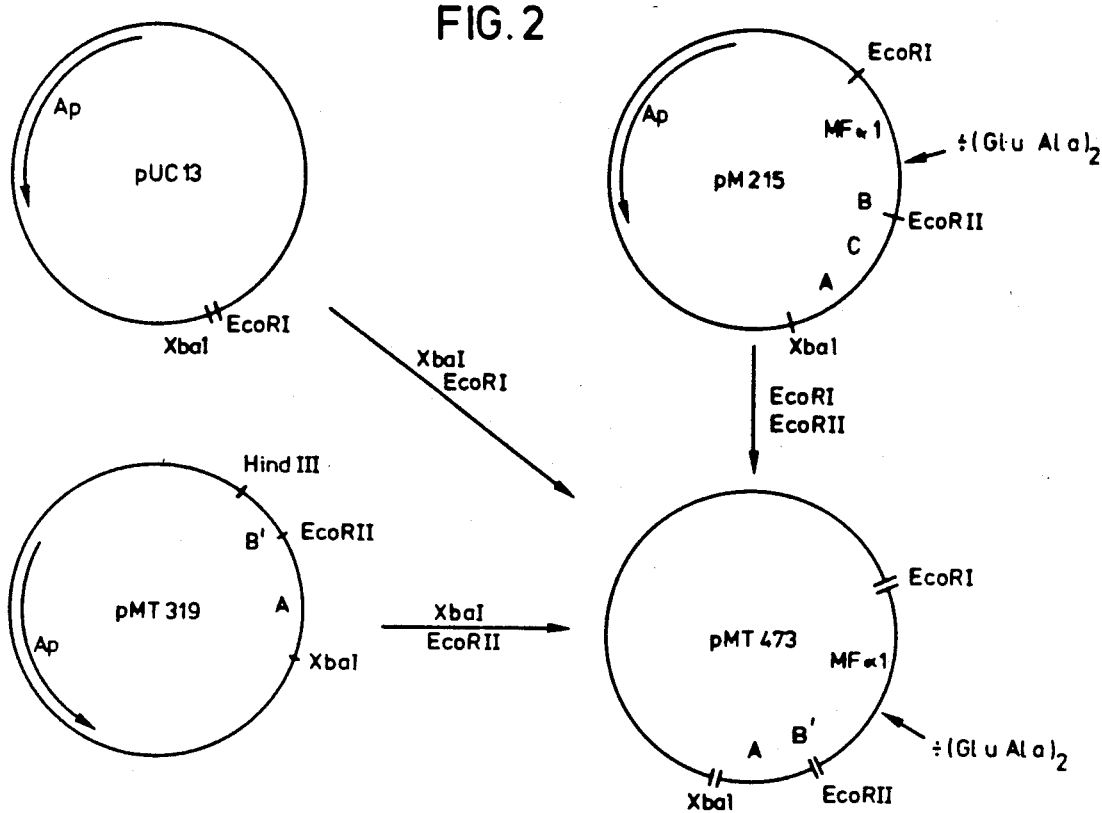
FIG. 2 illustrates the preparation of plasmid pMT475.
Figure 2:
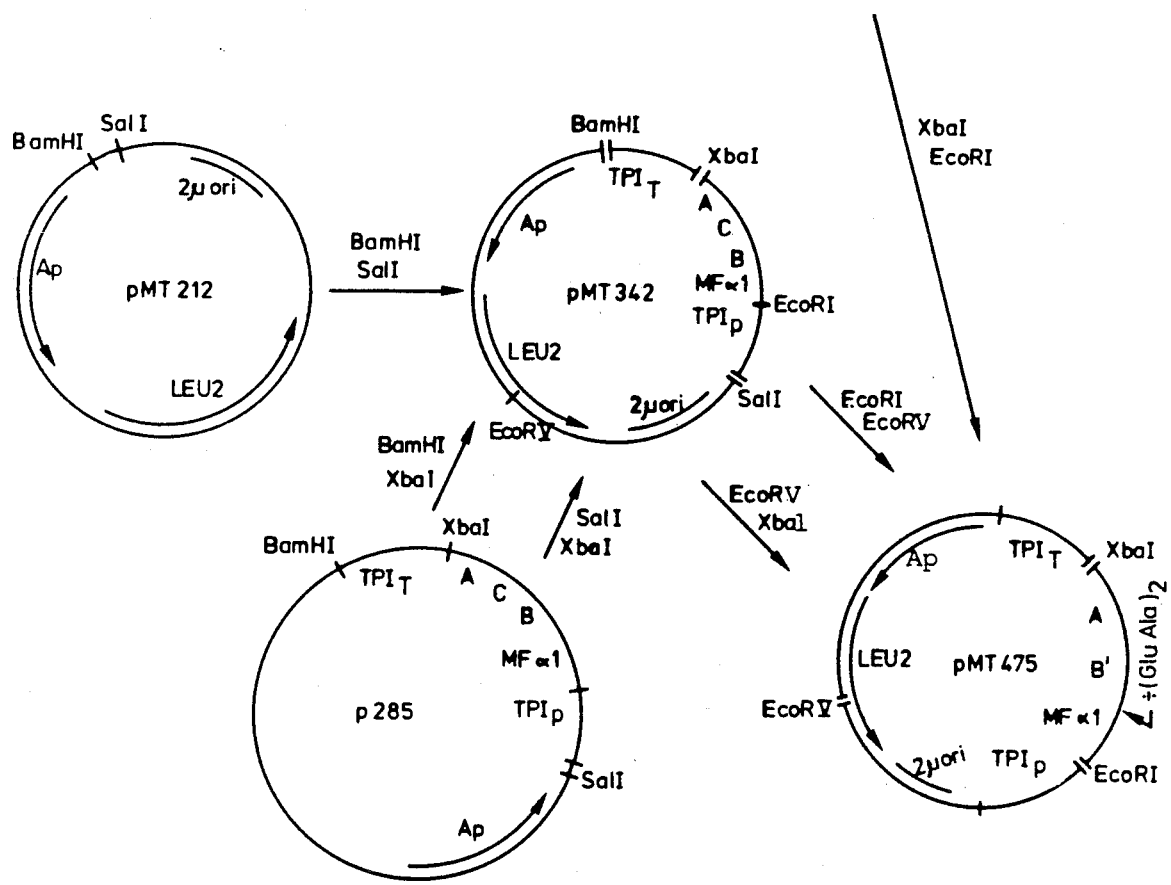
Figure 3:
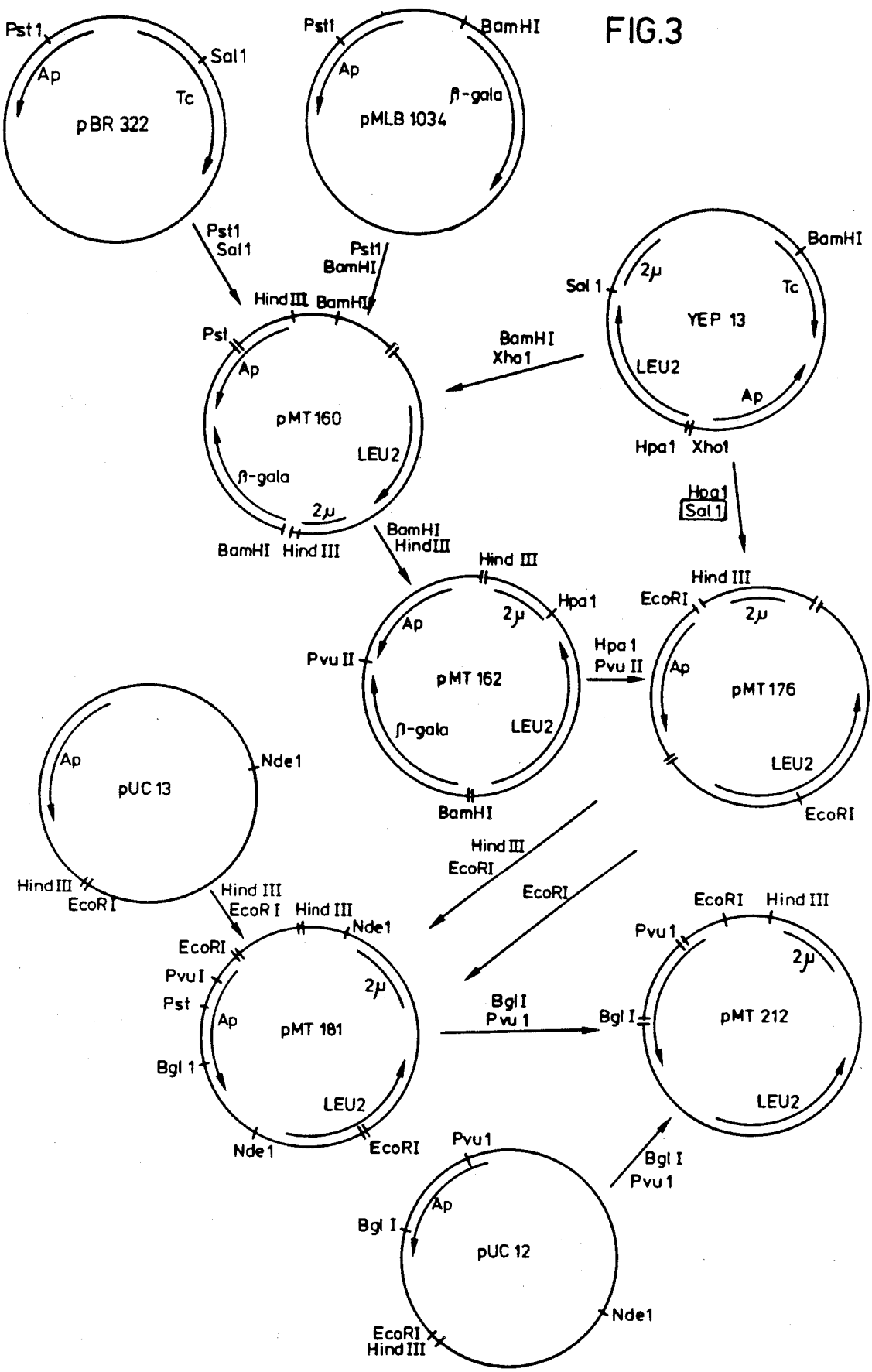
FIG. 3 illustrates the preparation of plasmid pMT212.

Construction of a yeast plasmid pMT475 for expression of B(1-29)-A(1-21) of human insulin (B'A) after a modified MFα1 leader To construct a plasmid for the expression of B'A after a MFα1 leader (J. Kurjan and I. Herskowitz, Structure of a Yeast Pheromone Gene (MFα): A Putative α-Factor Precursor Contains four Tandem Copies of Mature α-Factor. Cell 30 (1982) 933–943) lacking its last four amino acids (Glu-Ala-Glu-Ala), the 0.14 kb XbaI-EcoRII fragment containing the A and part of the B' sequences was isolated from pMT319. Likewise the 5' proximal part of the B' gene was isolated as a 0.36 kb EcoRI-EcoRII fragment from pM215. Plasmid pM215 was constructed by subcloning the EcoRI-XbaI fragment containing the proinsulin B-C-A gene from p285 into pUC13 (constructed as described for pUC8 and pUC9 by Vieira et al., Gene 19: 259–268 (1982)) and subsequent in vitro loopout removal of the 12 bases coding for Glu-Ala-Glu-Ala at the junction between MFα1 leader and proinsulin B-C-A gene. These two pieces covering the B'A gene were ligated to EcoRI-XbaI digested pUC13 vector (see FIG. 2) to give pMT473. The modified gene contained within a 0.5 kb EcoRI-XbaI fragment was isolated from pMT473 and then ligated to two fragments (4.3 kb XbaI-EcoRV and 3.3 kb EcoRV-EcoRI) from pMT342, pMT342 is the yeast vector pMT212 with an inserted $TPI_P$-MFα1 leader -B-C-A- $TPI_T$. The resulting plasmid, pMT475, contains the insert: $TPI_P$-MFα1 leader (minus Glu-Ala-Glu-Ala) -B'A-$TPI_T$. The construction of plasmids pMT342, pMT473 and pMT475 is outlined in FIG. 2. The construction of the vector pMT212 is shown in FIG. 3. Plasmid pMLB1034 is described by M. L. Berman et al., Advanced Bacterial Genetics, Cold Spring Harbor (1982), 49–51 and pUC12 was constructed as described for pUC13 (Vieira et al, ibid.).

EXAMPLE 4

Insertion of the B(1-29)-A(1-21) (B'A) gene into a stable yeast plasmid pMT479

Figure 4:
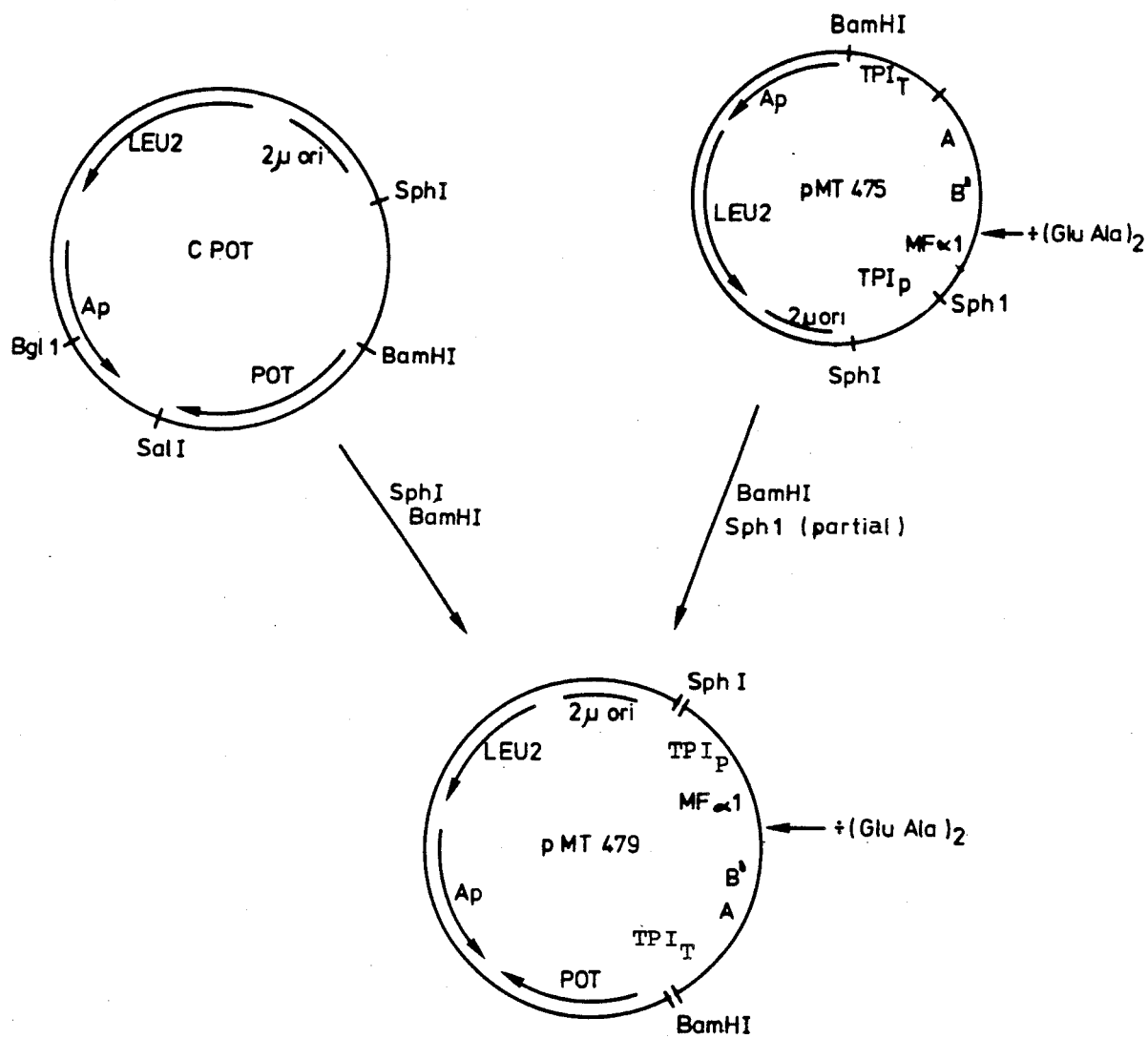
FIG. 4 illustrates the preparation of plasmid pMT479
Figure 5:
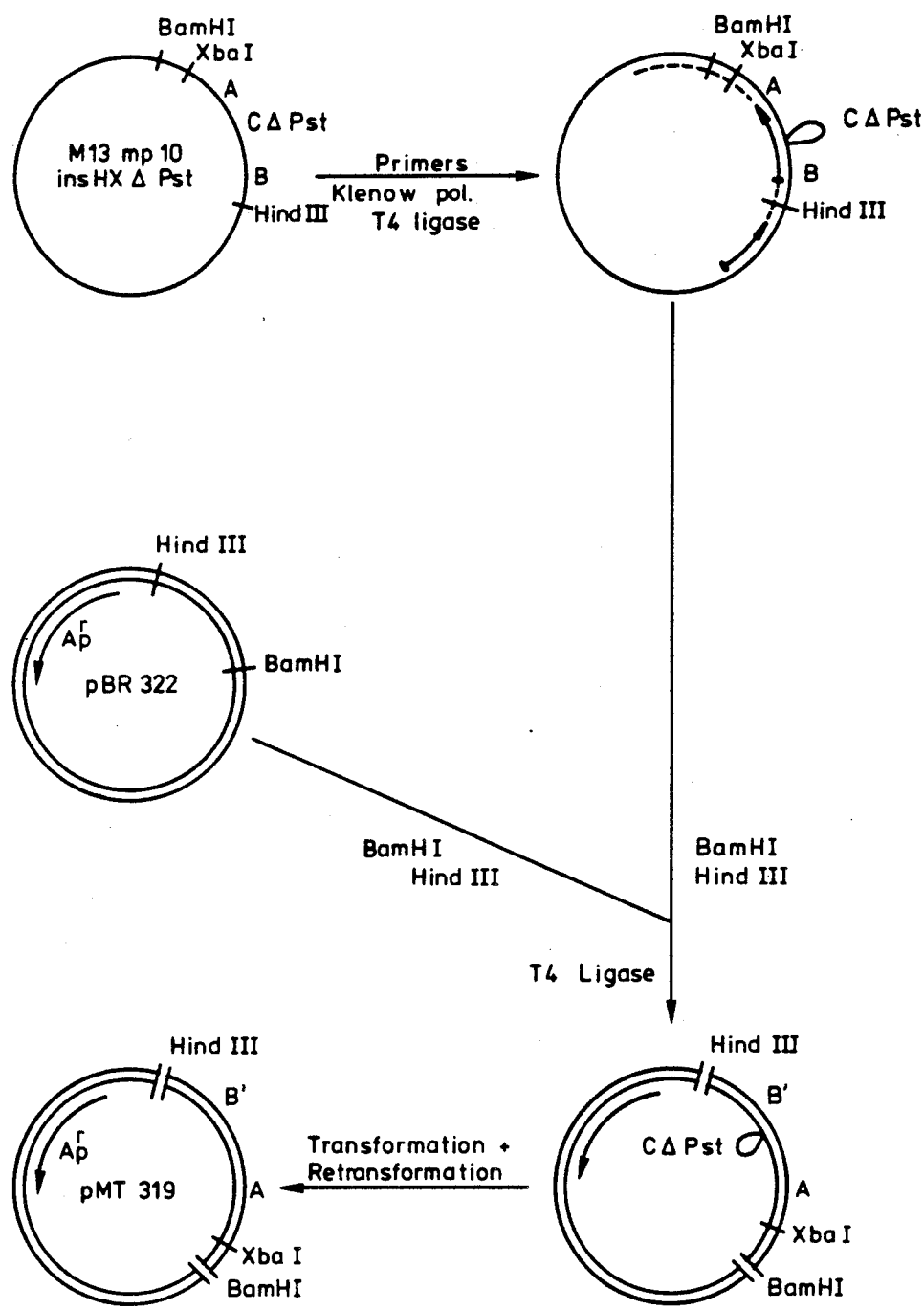
FIG. 5 illustrates the preparation of plasmid pMT319.
Figure 6:
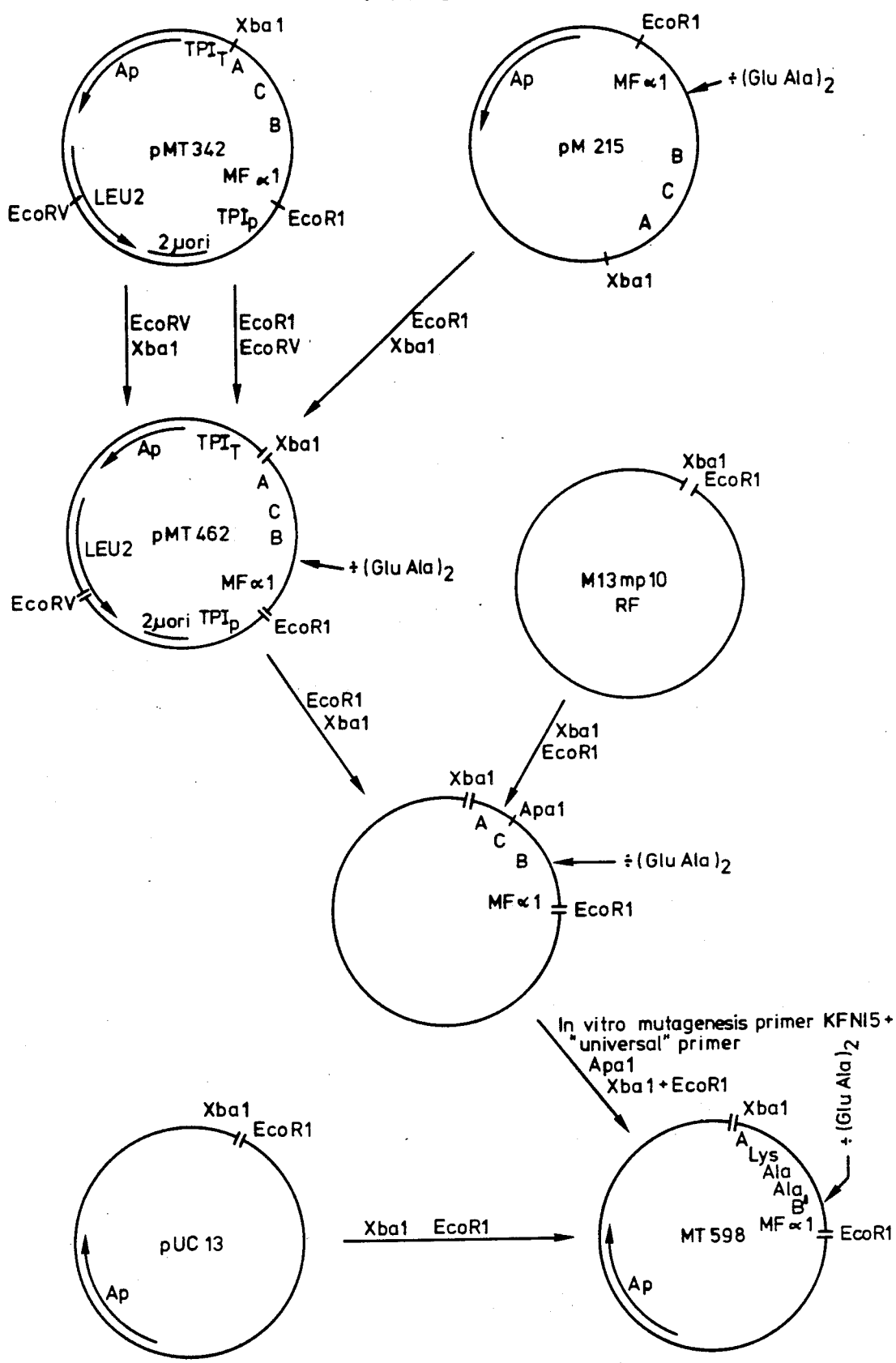
FIG. 6 illustrates the preparation of plasmid pMT598.
Figure 7:
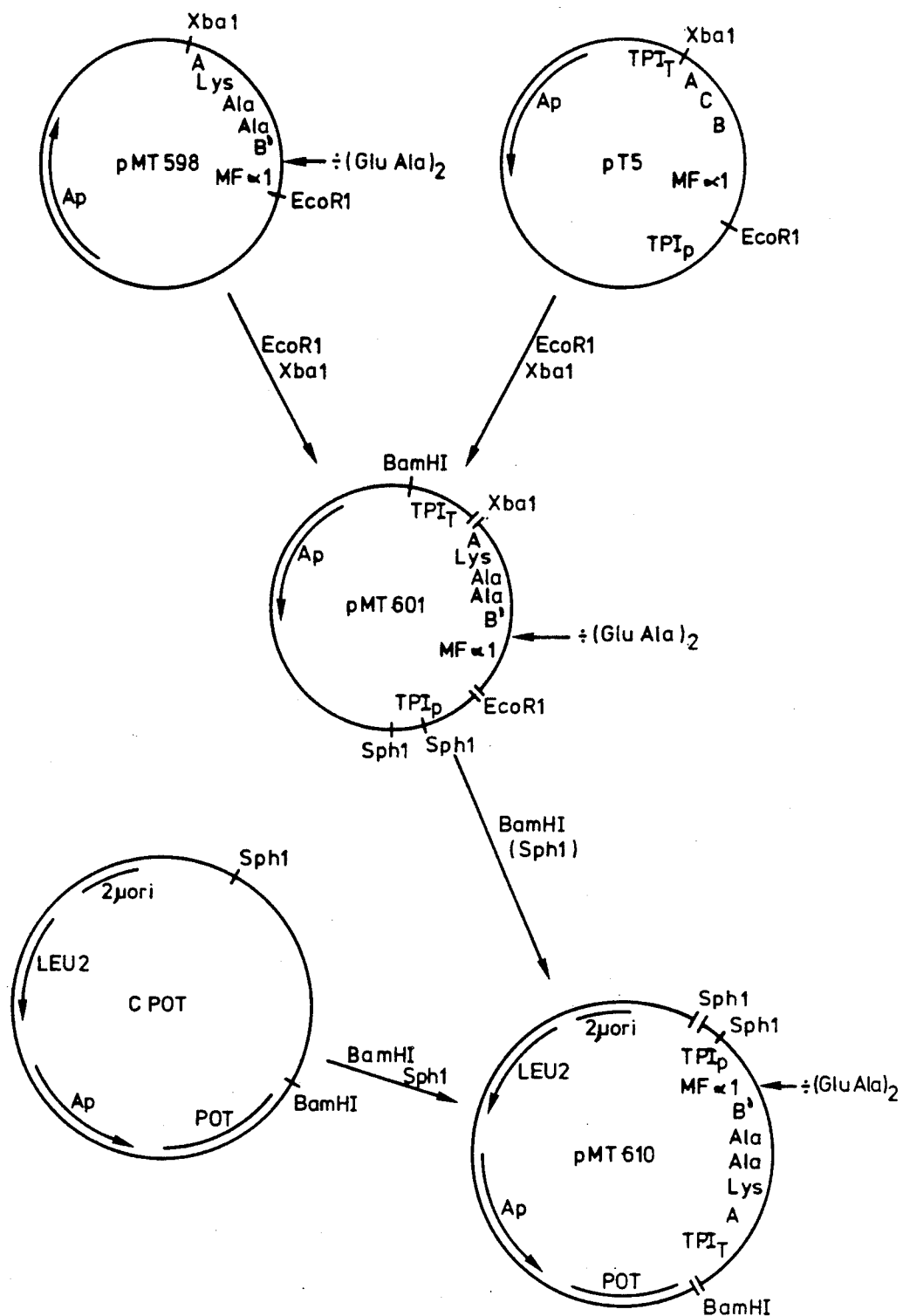
FIG. 7 illustrates the preparation of plasmid pMT610.

The modified B'A gene from pMT475 was isolated as a 2.1 kb BamHI-partial SphI fragment and ligated to an approximately 11 kb BamHI-SphI fragment of plasmid CPOT (ATCC No. 39685) to give plasmid pMT479 (FIG. 4). Plasmid CPOT is based on the vector C1/1 which has been modified by substituting the original pBR322 BglI-BamHI fragment with the similar BglI-BamHI fragment from pUC13 and subsequent insertion of the S.pombe TPI gene (POT) (U.S. patent application Ser. No. 614,734 filed on May 25, 1984) as a BamHI-SalI fragment to give CPOT. C1/1 is derived from pJDB 248, Beggs et al., Nature 275, 104–109 (1978) as described in EP patent application 0103409A.

EXAMPLE 5

Transformation

S. cerevisae strain MT118 (a, leu 2, ura 3, trp 1) was grown on YPD medium (Sherman et al., Methods in Yeast Genetics, Cold Spring Harbor Laboratory, 1981) to an $OD_{600}$ of 2.1 100 ml of culture was harvested by centrifugation, washed with 10 ml of water, recentrifuged and resuspended in 10 ml of (1.2M sorbitol, 25 mM Na₂EDTA pH=8.0, 6.7 mg/ml dithiotreitol). The suspension was incubated at 30° C. for 15 minutes, centrifuged and the cells resuspended in 10 ml of (1.2M sorbitol, 10 mM Na₂EDTA, 0.1M sodium citrate pH=5.8, 2 mg Novozym ® 234 enzyme). The suspension was incubated at 30° C. for 30 minutes, the cells collected by centrifugation, washed in 10 ml of 1.2M sorbitol and in 10 ml of CAS (1.2M sorbitol, 10 mM CaCl₂, 10 mM Tris (Tris=Tris(hydroxymethyl)-aminometan) pH=7.5) and resuspended in 2 ml of CAS. For transformation 0.1 ml of CAS-resuspended cells were mixed with approximately 1 µg of plasmid pMT344 and left at room temperature for 15 minutes. 1 ml of (20% polyethylenglycol 4000, 10 mM CaCl₂, 10 mM Tris pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl₂, 14 µg/ml leucine) and incubated at 30° C. for 2 hours. The suspension was then centrifuged and the pellet resuspended in 0.5 ml of 1.2M sorbitol. 6 ml of top agar (the SC medium of Sherman et al., (Methods in Yeast Genetics, Cold Spring Harbor Laboratory, 1981) with leucine omitted and containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant MT350 (=MT 118/pMT344) was chosen for further characterization.

Plasmid pMT475 was transformed into S. cerevisiae strain MT 362 (α, leu2) by the same procedure as above, and the transformant MT371 (=MT362/pMT475) isolated.

Transformation of pMT479 into strain E2-7BXE11-3C (a/α, Δtpi/Δtpi, pep 4-3/pep 4-3; this strain will be referred to as MT501) was performed as above with the following modifications: 1) prior to transformation strain MT501 was grown on YPGaL (1% Bacto yeast extract, 2% Bacto peptone, 2% galactose, 1% lactate) to an OD₆₀₀ of 0.6. 2) the SOS solution contained YPGaL instead of YPD. One transformant MT519 (=MT501/pMT479) was chosen for further characterization.

The transformed microorganisms MT 350, MT 371 and MT 519 were deposited by the applicant with Deutsche Sammlung von Mikroorganismen (DSM), Griesebachstrasse 8, D-3400 Göttingen, on May 15, 1984 and accorded the reference numbers DSM 2957, DSM 2958, and DSM 2959, respectively.

EXAMPLE 6

Expression of B(1-29)-A(1-21) insulin in yeast

Strains MT350 (DSM 2957) and MT371 (DSM 2958) were grown in synthetic complete medium SC (Sherman et al., Methods in Yeast Genetics, Cold Spring Harbor Laboratory 1981) with leucine omitted. For each strain, two 1 liter cultures in 2 liter baffled flasks were shaken at 30° C. until they reached OD$_{600nm}$ of 7 to 10. They were then centrifuged and the supernatant removed for further analysis.

Strain MT519 (DSM 2959) was grown similarly but on YPD medium (Sherman et al., Methods in Yeast Genetics, Cold Spring Harbor Laboratory, 1981) and to an OD$_{600nm}$ of 15, centrifuged and the supernatant separated for analysis as above.

EXAMPLE 7

Expression of B(1-29)-A(1-21) insulin in yeast strain MT350 (DSM 2957)

Yeast strain MT350 (DSM 2957) was grown as previously described in example 6 and expression products from 1100 ml of supernatant from this strain were isolated as follows:

10 g of LiChroprep ® RP-18 (Merck, art. 9303) were washed 3 times with 50 mM NH₄HCO₃, 60% EtOH and thereafter packed in a 6×1 cm column. The column was equilibrated with 50 ml of 50 mM NH₄HCO₃. 55 ml of 96% EtOH were added to 1100 ml of the yeast supernatant, and the mixture was applied to the column overnight (flow: 70 ml/h).

The column was washed with 10 ml of 0.5M NaCl and 10 ml of H₂O, and the peptides were eluted with 50 mM of NH₄HCO₃, 60% EtOH. The eluate (5 ml) was concentrated by vacuum centrifugation to 1.4 ml (to remove the ethanol), and the volume was adjusted to 10 ml with 25 mM of HEPES buffer pH=7.4. The sample was applied to an antiinsulin immunoabsorption column (AIS column) (2.5×4.5 cm) which had been washed 4 times with 5 ml of NaFAM-buffer (Heding, L., Diabetologia 8, 260-66, 1972) and twice with 5 ml of 25 mM HEPES-buffer prior to the application. After the application, the column was allowed to stand for 30 min. at room temperature and was thereafter washed 10 times with 4 ml of 25 mM HEPES buffer. The peptides were eluted with 20% HAc. The pH value of the eluate was adjusted to 7.0 with NH₄OH, and the pool was concentrated to 500 µl by vacuum rotation.

The sample from the previous step was further purified on HPLC on a 10µ Waters µBondopak C-18 column (3.9×300 mm). The A and B buffers were 0.1% TFA in H₂O and 0.70% TFA in MeCN, respectively. The column was equilibrated with 25% B (flow: 1.5 ml/min.) and the peptides were eluted with a linear gradient of MeCN (1%/min.) and detected at 276 nm. The yield in each step of the purification was determined by radioimmunoassay as previously described, and Table 2 summarizes the purification. The overall yield was 68%.

TABLE 2

| Purification of expression products from yeast strain MT350 supernatant | | |
|---|---|---|
| Purification step | Volume (ml) | Immunoreactive B(1-29)-A(1-21) insulin (nmol) |
| Supernatant | 1100 | 110$^x$ |
| RP-18 | 10 | 116 |
| Anti-insulin Sepharose | 0.5 | 116 |
| HPLC | 2.5 | 75 |

$^x$Dilution effect was observed in this sample

Only one peak containing immunoreactive B(1-29)-A(1-21) insulin material was detected from the HPLC column. Peptide material from this peak was isolated and subjected to amino acid sequence analysis. The sequence analysis was performed with a Gas Phase sequencer (Applied Biosystem Model 470A) as described by Hewick, R. M. et al. (J. Biol. Chem. 256, 7990-7997, 1981). From the sequencing results it could be concluded that the expression products consisted of 3 peptides:

| | |
|---|---|
| (Glu—Ala)$_2$-B(1-29)-A(1-21) insulin | 89% |
| Glu—Ala-B(1-29)-A(1-21) insulin | 2% |
| B(1-29)-A(1-21) insulin | 9% |

The peptides were present in the relative amount as indicated.

EXAMPLE 8

Expression of B(1-29)-A(1-21) insulin in yeast strain MT371 (DSM 2958)

Yeast strain MT371 (DSM 2958) was grown as previously described in example 6 and expression products from 665 ml of supernatant from this strain were isolated as described in Example 7. The overall yield was 50 mmol, corresponding to 39%. Peptide material was isolated from the HPLC column and sequenced as described in Example 7. From the sequence results (18 residues from the N-terminal) it could be concluded that the peptide was homogeneous B(1-29)-A(1-21) insulin.

Comparison of these results to the results obtained in Example 7 indicates the advisability of removing the Glu-Ala-Glu-Ala sequence from the C-terminal of the MFα1 leader. It appears from Example 7 that the yeast dipeptidase enzyme does not function very efficiently in splitting off the Glu-Ala and Glu-Ala-Glu-Ala from the B(1-29)-A(1-21) insulin prior to secretion of the insulin precursor from the yeast cells.

EXAMPLE 9

Expression of B(1-29)-A(1-21) insulin in yeast strain MT519 (DSM 2959)

Yeast strain MT519 (DSM 2959) was grown as previously described in example 6 and expression products from 70 ml of supernatant were isolated as described in example 7. The overall yield was 116 mmol, corresponding to 57%. The peptide was sequenced as described in example 7. As judged from the 42 residues identified from the N-terminal end, the peptide was homogeneous B(1-29)-A(1-21) insulin. Approximately 5 nmol of peptide was hydrolyzed in 100 μl 6N HCl for 24 h at 110° C. The hydrolysate was analyzed on a Beckman Model 121M amino acid analyser. The following amino acid composition was found:

TABLE 3

Amino acid analysis of purified B(1-29)-A(1-21) insulin

| Amino acid | Found | Theoret. | Amino acid | Found | Theoret. |
|---|---|---|---|---|---|
| Asx* | 2.97 | 3 | Val | 3.37 | 4 |
| Thr | 1.77 | 2 | Ile | 1.65 | 2 |
| Ser | 2.45 | 3 | Leu* | 5.65 | 6 |
| Glx* | 6.68 | 7 | Tyr | 3.51 | 4 |
| Pro | 1.33 | 1 | Phe* | 2.73 | 3 |
| Gly* | 3.95 | 4 | Lys* | 0.95 | 1 |
| Ala* | 1.22 | 1 | His* | 1.84 | 2 |
| Cys 0.5 | 4.54 | 6 | Arg* | 1.13 | 1 |

*amino acid used for normalization.

EXAMPLE 10

Construction of a yeast plasmid pMT610 for expression of B(1-29)-Ala-Ala-Lys-A(1-21)

Figure 8:
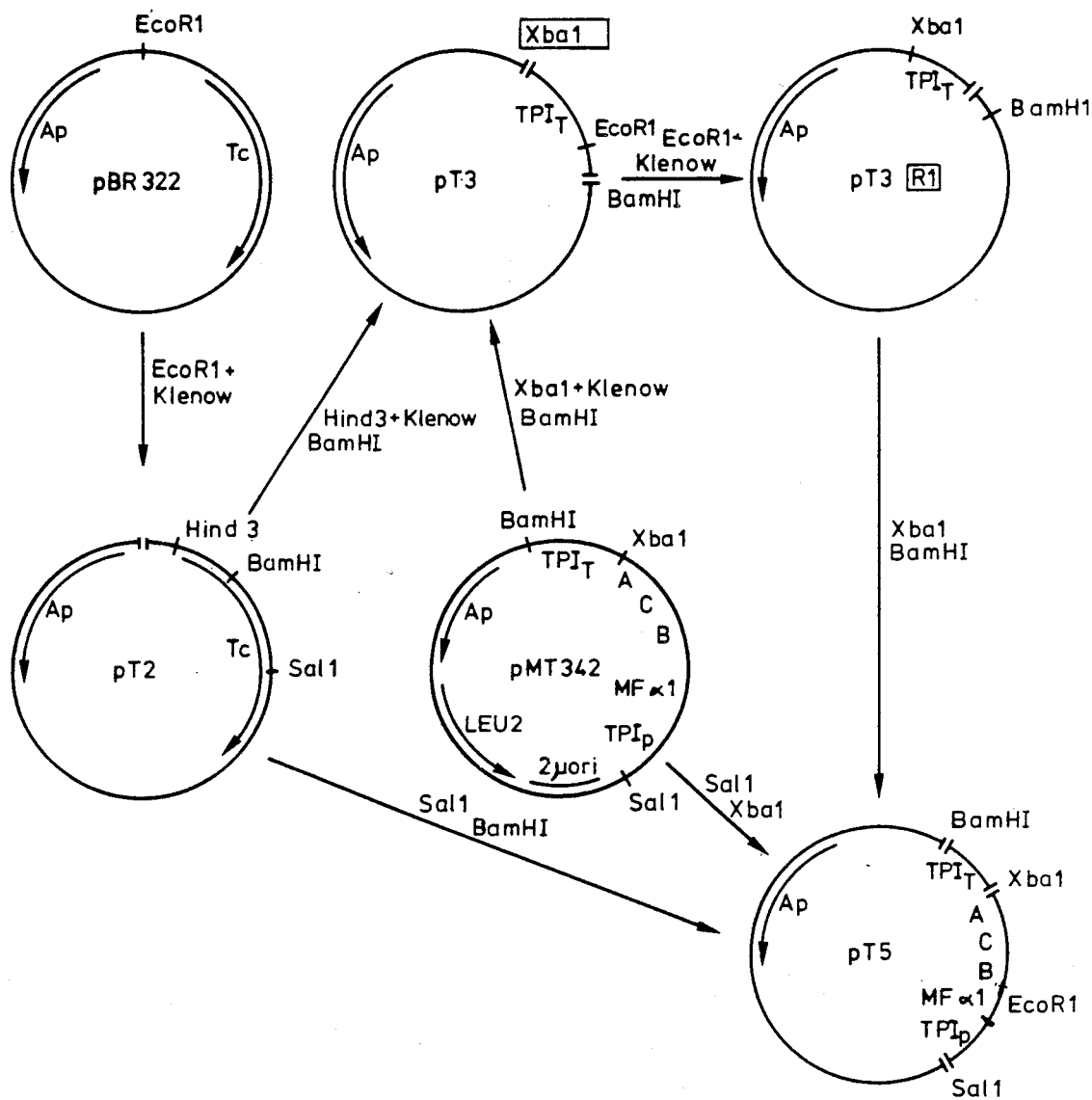
FIG. 8 illustrates the preparation of plasmid pT5.

A 4.3 kb EcoRV-Xbal and a 3.3 kb EcoRI-EcoRV fragment from pMT342 (see example 3) were ligated to a 0.6 kb EcoRI-Xbal fragment of pM215 (see example 3). The obtained plasmid pMT462 harbours the insert MFα1 leader (minus Glu-Ala-Glu-Ala)-B-C-A. For converting the B-C-A encoding fragment into a B(1-29)-Ala-Ala-Lys-A(1-21) encoding fragment the modified site specific mutagenesis procedure (K. Norris et al., ibid.) was used. A 0.6 kb EcoRI-Xbal fragment from pMT462 encoding MFα1 leader (minus Glu-Ala-Glu-Ala)-B-C-A was inserted into M13 mp10 RF phage cut with Xbal-EcoRI. Single strand M13 phage containing the above EcoRI-Xbal insert was incubated with a 30mer d(TTCACAATGCCCT-TAGCGGCCTTGGGTGTG) primer (KFN15) and the "universal" 15-mer M13 primer d(TCCCAGT-CACGACGT) (see example 1), heated to 90° C. for 5 minutes and slowly cooled to room temperature in order to allow annealing. Then partly double stranded DNA was made by addition of a d-NTP-mix, Klenow Polymerase and T4 ligase. After phenol extraction, ethanol precipitation and resuspension, the DNA was cut with restriction enzymes Apal, Xbal and EcoRl. After another phenol extraction, ethanol precipitation and resuspension, the DNA was ligated to EcoRl-Xbal cut pUC13. The ligation mixture was transformed into an E. coli (r⁻m⁺) strain and plasmids were prepared from a number of transformants. Plasmid preparations were cut with EcoRl and Xbal and those preparations showing bands at both 0.5 and 0.6 kb were retransformed into E. coli. From the retransformation a transformant harbouring only pUC13 with a 0.5 kb insert was selected. The sequence of the EcoRI-Xbal insert of this plasmid, pMT598, was then confirmed by the Maxam-Gilbert method to encode MFα1 leader (minus Glu-Ala-Glu-Ala)-B(1-29)-Ala-Ala-Lys-A(1-21). The Xbal-EcoRI insert from pMT598 was provided with TPI promotor and TPI terminator by ligation of a 0.5 kb Xbal-EcoRI fragment of pMT598 with a 5.5 kb Xbal-EcoRI fragment of pT5. The construction of pT5 harbouring the insert TPIp-MFα1 leader B-C-A-TPI$_T$ is illustrated in FIG. 8. The resulting plasmid pMT 601 containing the insert TPIp-MFα1 leader (minus Glu-Ala-Glu-Ala)-B(1-29)-Ala-Ala-Lys-A(1-21)-TPI$_T$ was cut with BamHl and partially with Sphl and the 2.1 kb fragment was inserted in CPOT cut with BamHl and Sphl. The resulting plasmid pMT610 was used for transformation of yeast.

EXAMPLE 11

Construction of a yeast plasmid pMT639 for expression of B(1-29)-Ser-Lys-A(1-21)

Figure 9:
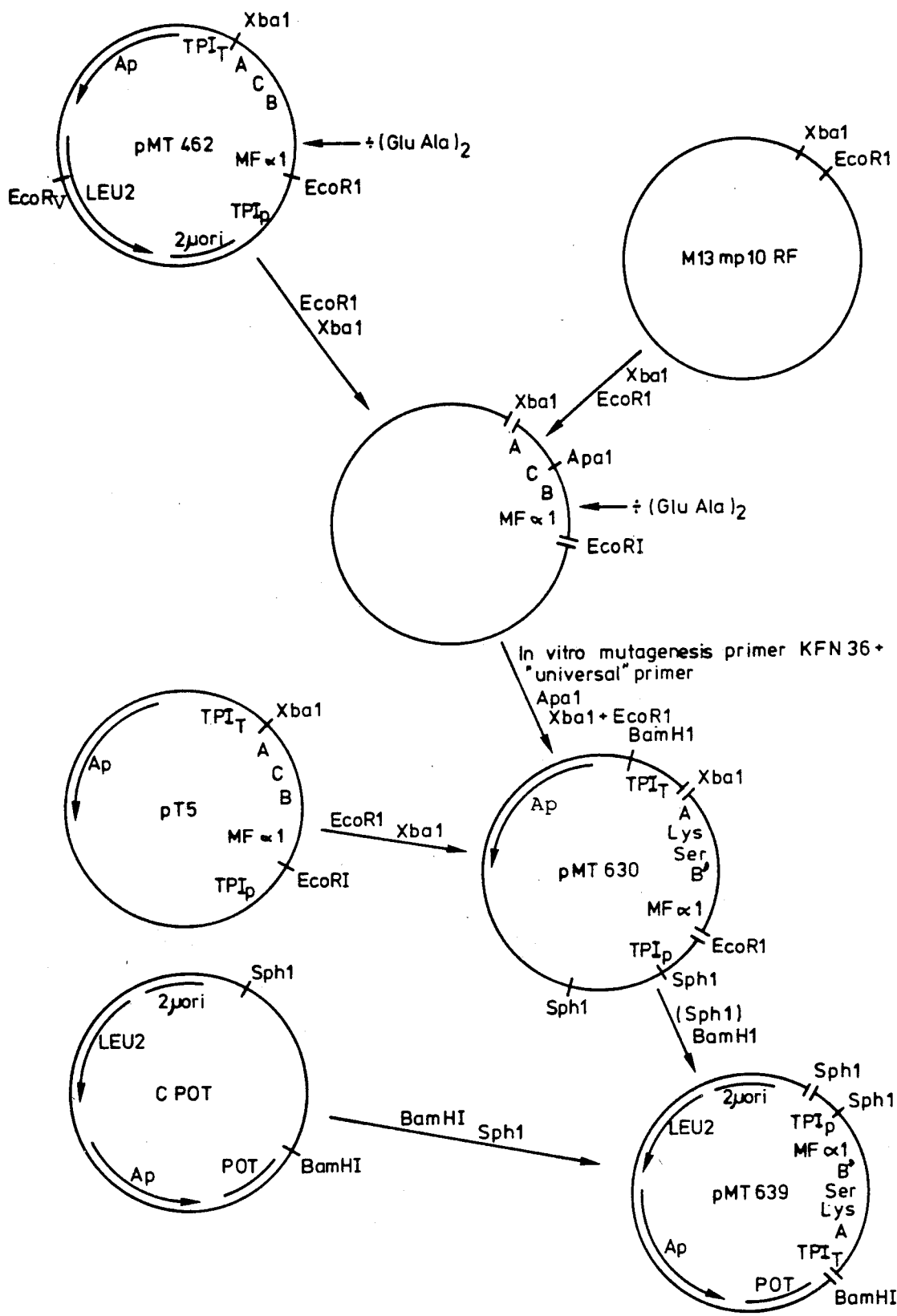
FIG. 9 illustrates the preparation of plasmid pMT639.

The BCA encoding fragment from pMT462 (see example 10) was converted into B(1-29)-Ser-Lys-A(1-21) by a procedure analogous with the procedure described in example 10 by site specific mutagenesis with a mixture of 27-mer d(TCCACAATGCCCT-TAGACTTGGGTGTG) primer KFN36 and the "universal" 15-mer M13 primer. After filling in with Klenow polymerase and ligation with T4 ligase the partly double stranded DNA was digested with Apal, EcoRI and Xbal and ligated with the 5.5 kb Xbal-EcoRI fragment from plasmid pT5 (see example 10). After transformation and retransformation into E. coli, a plasmid pMT 630 containing the insert MFα1 leader (minus Glu-Ala-Glu-Ala)-B(1-29)-Ser-Lys-A(1-21) was isolated and the sequence of the insert confirmed. The further procedure for obtaining plasmid pMT639 containing the insert TPIp-MFα1 (minus Glu-Ala-Glu-Ala)-B(1-29)-Ser-Lys-A(1-21)-TPI$_T$ was as described in example 10. The construction of pMT639 is illustrated in FIG. 9.

EXAMPLE 12

Expression of B(1-29)-Ala-Ala-Lys-A(1-21) in yeast strain MT 620

*S. cerevisiae* strain MT501 (see example 5) was transformed with pMT 610 as described for pMT479 in example 5. Transformant colonies were picked after 3 days at 30° C., reisolated and used to start liquid cultures. One such transformant MT 620=(MT501/pMT610) was chosen for further characterization. MT620 was deposited by the applicant with Deutsche Sammlung von Mikroorganism (DSM), on Jan. 16, 1985 and accorded the reference number DSM 3196.

MT 620 was grown on YPD medium. A two liter culture in 2 liter baffled flask was shaken at 30° C. to an $OD_{600nm}$ of 15. After centrifugation the supernatant was removed for further analysis. The expression level determined by radioimmunoassay was 1.2 μmol/l. Expression products from 840 ml of supernatant were purified as described in Example 7. (RP-18 column, Anti-insulin Sepharose and HPLC). The overall yield was 100 nmol corresponding to about 10%. Peptide material was isolated from the HPLC-column and sequenced as described in Example 7. 35 Edman degradation cycles were carried out (Table 4). From the sequence results the position of the 3 amino acid residue chains (Ala-Ala-Lys) separating the B(1-29) and the A(1-21) chains was confirmed (see table 4).

TABLE 4

Sequence analysis of B(1-29)-Ala—Ala—Lys-A(1-21) isolated from the culture medium of strain MT 620.

| Cyclus No. | PTH-amino acid residue | Yield (pmol) |
|---|---|---|
| 1 | Phe | 3381 |
| 2 | Val | 1738 |
| 3 | Asn | 5169 |
| 4 | Gln | 2750 |
| 5 | His | 2045 |
| 6 | Leu | 1405 |
| 7 | Cys | — |
| 8 | Gly | 1372 |
| 9 | Ser | 345 |
| 10 | His | 1105 |
| 11 | Leu | 2228 |
| 12 | Val | 1963 |
| 13 | Glu | 1219 |
| 14 | Ala | 1514 |
| 15 | Leu | 1793 |
| 16 | Tyr | 1707 |
| 17 | Leu | 1354 |
| 18 | Val | 1765 |
| 19 | Cys | — |
| 20 | Gly | 882 |
| 21 | Glu | 1019 |
| 22 | Arg | 1100 |
| 23 | Gly | 1123 |
| 24 | Phe | 1492 |
| 25 | Phe | 2042 |
| 26 | Tyr | 1014 |
| 27 | Thr | 195 |
| 28 | Pro | 710 |
| 29 | $B_{29}$Lys | 1173 |
| 30 | Ala | 1026 |
| 31 | Ala | 885 |
| 32 | Lys | 1175 |
| 33 | $A_1$Gly | 552 |
| 34 | Ile | 518 |
| 35 | Val | 548 |

The average repetitive yield was 95.6%.

EXAMPLE 13

Expression of B(1-29)-Ser-Lys-A(1-21) in yeast strain MT643

*S. cerevisiae* strain MT501 was transformed with pMT639 as described for pMT479 in example 5.

One transformant MT643=(MT501/pMT639) was chosen for further characterization. MT643 was deposited by the applicant at DSM on Jan. 16, 1985 and accorded the reference No. DSM 3197.

MT643 was grown as described in example 12. After centrifugation the supernatant was removed for further analysis.

The expression level of the insulin precursor determined by radioimmunoassay was 1.6 μmol/l. Expression products from the supernatant from strain MT 643 was isolated as described in Example 7. The peptide material isolated from the HPLC column was submitted to sequence analysis as described in Example 7. From the sequence results (not shown) the position of the two amino acid residues chains (Ser-Lys) separating the B(1-29) and A(1-21) chains was confirmed.

EXAMPLE 14

Conversion of B(1-29)-A(1-21) to Thr(Bu$^t$)-OBu$^t$(B30) human insulin 20 mg of B(1-29)-A(1-21) was dissolved in 0.1 ml of 10M acetic acid. 0.26 ml of 1.54M Thr(Bu$^t$)-OBu$^t$ in N,N-dimethylacetamide was added. The mixture was cooled to 12° C. 2.8 mg of trypsin dissolved in 0.035 ml of 0.05M calcium acetate was added. After 72 hours at 12° C., the proteins were precipitated by addition of 4 ml of acetone, isolated by centrifugation and dried in vacuo. The conversion of B(1-29)-A(1-21) to Thr(Bu$^t$)-OBu$^t$(B30) human insulin was 64% by HPLC.

EXAMPLE 15

Conversion of B(1-29)-A(1-21) to Thr-OMe(B30) human insulin 20 mg of B(1-29)-A(1-21) was dissolved in 0.1 ml of 10M acetic acid. 0.26 ml of 1.54M Thr-OMe in a mixture of dimethyl sulphoxide and butane-1,4 diol 1/1 (v/v) was added. 1 mg of lysyl endopeptidase from Achromobacter lyticus (Wako Pure Chemical Industries, Osaka, Japan) in 0.07 ml of water was added. After 120 hours at 25° C., the proteins were precipitated by addition of 4 ml of acetone, isolated by centrifugation, and dried in vacuo. The conversion of B(1-29)-A(1-21) to Thr-OMe(B30) human insulin was 75% by HPLC.

EXAMPLE 16

Conversion of B(1-29)-Ser Lys-A(1-21) to Thr-OBu$^t$(B30) human insulin 20 mg B(1-29)-Ser-Lys-A(1-21) was dissolved in 0.1 ml of a mixture of 34.3% acetic acid (v/v) and 42.2% N,N-dimethylformamide (v/v) in water. 0.2 ml of 2M Thr-OBu$^t$ as hydroacetate salt in N,N-dimethylformamide was added. The mixture was thermostated at 12° C. 2 mg of trypsin in 0.05 ml 0.05M calcium acetate was added. After 24 hours at 12° C., the proteins were precipitated by addition of 4 ml of acetone, isolated by centrifugation and dried in vacuo. The conversion of B(1-29)-Ser-Lys-A(1-21) to Thr-OBu$^t$(B30) human insulin was 85% by HPLC.

EXAMPLE 17

Conversion of B(1-29)-Ala-Ala-Lys-A(1-21) to Thr-OBu$^t$(B30) human insulin 20 mg B(1-29)-Ala-Ala-Lys-A(1-21) was dissolved in 0.1 ml of a mixture of 34.3% acetic acid (v/v) and 42.2% N,N dimethylformamide (v/v) in water. 0.2 ml of 2M Thr-OBu$^t$ as hydroacetate salt in N,N-dimethylformamide was added. The mixture was thermostated at 12° C. 2 mg of trypsin in 0.05 ml 0.05M calcium acetate was added. After 96 hours at 12° C., the proteins were precipitated by addition of 4 ml of acetone, isolated by centrifugation and dried in vacuo. The conversion of B(1-29)-Ala-Ala-Lys-A(1-21) to Thr-OBu$^t$(B30) human insulin was 84% by HPLC.

EXAMPLE 18

Preparation of human insulin from various human insulin esters

The human insulin esters in the crude acetone precipitates were purified by gelfiltration and anion exchange chromatography as described in Methods in Diabetes Research vol. 1, p. 407-408 (Eds. J. Larner and S. Pohl (John Wiley Sons, New York, 1984)). The method was applicable to any of the 3 human insulin esters. The cleavages of the various ester groups, rendering human insulin in nearly 100% yields, were carried out by hydrolysis of Thr-OMe(B30) human insulin and by acidolysis with trifluoroacetic acid of Thr(Bu$^t$)-OBu$^t$(B30) human insulin and of Thr-OBu$^t$(B30) human insulin as described ibid. p. 409.

We claim:

1. A DNA-sequence comprising a sequence encoding an insulin precursor of the formula:

B(1-29)-(X$_n$-Y)$_m$-A(1-21), wherein X$_n$ is a peptide chain with n amino acid residues, Y is Lys or Arg, n=0 to 33, m=0 or 1, B(1-29) is a shortened B-chain of human insulin from Phe$^{B1}$ to Lys$^{B29}$, A(1-21) is the A-chain of human insulin, and the peptide chain —X$_n$-Y- does not contain two adjacent basic amino acid residues.

2. A DNA-sequence according to claim 1 wherein m is 0.

3. A DNA-sequence according to claim 1 wherein m is 1 and n is 1-8.

4. A DNA-sequence according to claim 1 wherein said insulin precursor is

B(1-29)-Ala-Ala-Lys-A(1-21).

5. A DNA-sequence according to claim 1 wherein said insulin precursor is B(1-29)-Ser-Lys-A(1-21).

6. A replicable expression vehicle capable of expressing in yeast a DNA-sequence encoding an insulin precursor of the formula B(1-29)-(X$_n$-Y)$_m$-A(1-21), wherein X$_n$ is a peptide chain with n amino acid residues, Y is Lys or Arg, n=0 to 33, m=0 or 1, B(1-29) is a shortened B-chain of human insulin from Phe$^{B1}$ to Lys$^{B29}$, A(1-21) is the A-chain of human insulin, and the peptide chain —X$_n$-Y- does not contain two adjacent basic amino acids.

7. A replicable expression vehicle according to claim 6 comprising the plasmid pMT344.

8. A replicable expression vehicle according to claim 6 comprising the plasmid pMT475.

9. A replicable expression vehicle according to claim 6 comprising the plasmid pMT479.

10. A replicable expression vehicle according to claim 6 comprising the plasmid pMT610.

11. A replicable expression vehicle according to claim 6 comprising the plasmid pMT639.

12. A yeast strain transformed with a replicable expression vehicle capable of expression in yeast a DNA-sequence encoding an insulin precursor of the formula B(1-29)-(X$_n$-Y)$_m$-A(1-21), wherein X$_n$ is a peptide chain with n amino acid residues, Y is Lys or Arg, n=0 to 33, m=0 or 1, B(1-29) is a shortened B-chain of human insulin from Phe$^{B1}$ to Lys$^{B29}$, A(1-21) is the A-chain of human insulin, and the peptide chain —X$_n$-Y- does not contain two adjacent basic amino acids.

13. A yeast strain according to claim 12, wherein said replicable expression vehicle comprises the plasmid pMT344.

14. A yeast strain according to claim 12, wherein said replicable expression vehicle comprises the plasmid pMT475.

15. A yeast strain according to claim 12, wherein said replicable expression vehicle comprises the plasmid pMT479.

16. A yeast strain according to claim 12, wherein said replicable expression vehicle comprises the plasmid pMT610.

17. A yeast strain according to claim 12, wherein said replicable expression vehicle comprises the plasmid pMT639.

18. A process for producing an insulin precursor of the formula:

B(1-29)-(X$_n$-Y)$_m$-A(1-21), wherein X$_n$ is a peptide chain with n expressible amino acid residues, Y is Lys or Arg, n=0 to 33, m=0 or 1, B(1-29) is a shortened B-chain of human insulin from Phe$^{B1}$ to Lys$^{B29}$, A(1-21) is the A-chain of human insulin, and the peptide chain —X$_n$-Y- does not contain two adjacent basic amino acid residues; said process comprising the steps of:
culturing a transformant yeast strain in a suitable nutrient medium, said transformant yeast strain including a replicable expression vehicle capable of expressng a DNA-sequence encoding said insulin precursor, and recovering said insulin precursor.

19. A process for producing an insulin precursor according to claim 18, wherein said yeast strain is DSM 2957.

20. A process for producing an insulin precursor according to claim 19, wherein said insulin precursor has the formula B(1-29)-A(1-21).

21. A process for producing an insulin precursor according to claim 18, wherein said yeast strain is DSM 2958.

22. A process for producing an insulin precursor according to claim 21, wherein said insulin precursor according to claim 21, wherein said insulin precursor has the formula

B(1-29)-A(1-21).

23. A process for producing an insulin precursor according to claim 18, wherein yeast strain is DSM 2959.

24. A process for producing an insulin precursor according to claim 23, wherein said insulin precursor has the formula B(1-29)-A(1-21).

25. A process for producing an insulin precursor according to claim 18, wherein said yeast strain is DSM 3196.

26. A process for producing an insulin precursor according to claim 25, wherein said insulin precursor has the formula B(1-29)-Ala-Ala-Lys-A(1-21).

27. A process for producing an insulin precursor according to claim 18, wherein said yeast strain is DSM 3197.

28. A process for producing an insulin precursor according to claim 27, wherein said insulin precursor has the formula B(1-29)-Ser-Lys-A(1-21).

29. A process for preparing human insulin comprising the steps of:
transforming a yeast strain with a replicable expression vehicle capable of expressing a DNA-sequence encoding an insulin precursor of the formula B(1-29)-$(X_n$-Y$)_m$-A(1-21), wherein $X_n$ is a peptide chain with n expressible amino acid residues, Y is Lys or Arg, n=0 to 33, m=0 or 1, B(1-29) is a shortened B-chain of human insulin from $Phe^{B1}$ to $Lys^{B29}$, A(1-21) is the A-chain of human insulin, and the chain —$X_n$-Y- does not contain two adjacent basic amino acids;
culturing said transformed yeast strain in a suitable nutrient medium so that expression of said insulin precursor occurs;
recovering said expressed insulin precursor from said nutrient medium; and
converting said insulin precursor into human insulin.

30. Human insulin precursors of the general formula

B(1-29)-$X_n$-Y-A(1-21), wherein $X_n$ is a peptide chain with n expressible amino acid residues, n=0 to 33, Y is Lys or Arg, B(1-21) is a shortened B-chain of human insulin from $Phe^{B1}$ to $Lys^{B29}$, A(1-21) is the A-chain of human insulin, and the peptide chain —$X_n$-Y- does not contain two adjacent, basic amino acid residues.

31. A human insulin precursor according to claim 30 having the formula

B(1-29)-Ala-Ala-Lys-A(1-21).

32. A human insulin precursor according to claim 30 having the formula

B(1-29)-Ser-Lys-A(1-21).

* * * * *